US009168118B2

(12) United States Patent
Noel et al.

(10) Patent No.: US 9,168,118 B2
(45) Date of Patent: Oct. 27, 2015

(54) IMPLANTABLE ATTACHMENT DEVICE, IMPLANT FOR TREATING PROLAPSE OF THE PELVIC FLOOR COMPRISING SUCH A DEVICE AND KIT COMPRISING SAID DEVICE

(71) Applicant: COUSIN BIOTECH, Wervicq-Sud (FR)

(72) Inventors: Stéphane Noel, Hantay (FR); Farid Kamche, Tourcoing (FR); Gilles Solecki, Lannoy (FR)

(73) Assignee: COUSIN BIOTECH, Wervieq-Sud (FR)

( * ) Notice: Subject to any disclaimer, the term of this patent is extended or adjusted under 35 U.S.C. 154(b) by 241 days.

(21) Appl. No.: 13/893,370

(22) Filed: May 14, 2013

(65) Prior Publication Data
US 2013/0317287 A1    Nov. 28, 2013

(30) Foreign Application Priority Data

May 22, 2012    (FR) .................................... 12 54648

(51) Int. Cl.
*A61F 2/00*    (2006.01)
*A61B 17/06*   (2006.01)
*A61B 17/00*   (2006.01)
*A61B 17/04*   (2006.01)

(52) U.S. Cl.
CPC .......... *A61F 2/0022* (2013.01); *A61B 17/06109* (2013.01); *A61F 2/0045* (2013.01); *A61B 2017/00805* (2013.01); *A61B 2017/00831* (2013.01); *A61B 2017/0475* (2013.01)

(58) Field of Classification Search
CPC .. A61B 17/04; A61B 17/06; A61B 17/06109; A61B 2017/00805; A61B 2017/00831; A61B 2017/0475; A61F 2/08; A61F 2/0045; A61F 2/0022
USPC .................................................. 600/29–32, 37
See application file for complete search history.

(56) References Cited

U.S. PATENT DOCUMENTS

| 4,932,963 | A  | * | 6/1990 | Ritter et al. | .................. 606/224 |
| 6,296,659 | B1 | * | 10/2001 | Foerster | ....................... 606/224 |
| 8,123,671 | B2 |   | 2/2012 | Evans | |
| 2002/0077526 | A1 |   | 6/2002 | Kammerer et al. | |
| 2003/0176762 | A1 | * | 9/2003 | Kammerer | ...................... 600/30 |
| 2005/0131393 | A1 |   | 6/2005 | Chu et al. | |
| 2007/0055095 | A1 |   | 3/2007 | Chu et al. | |
| 2008/0082127 | A1 | * | 4/2008 | Stone et al. | .................. 606/232 |
| 2010/0016894 | A1 |   | 1/2010 | Houard et al. | |
| 2010/0312051 | A1 |   | 12/2010 | Brown | |

FOREIGN PATENT DOCUMENTS

WO    2005122721 A2    12/2005

* cited by examiner

*Primary Examiner* — Samuel Gilbert
(74) *Attorney, Agent, or Firm* — MH2 Technology Law Group, LLP

(57) ABSTRACT

The present invention relates to an implantable attachment device comprising an elongate element which is tubular flexible and hollow delimiting an internal volume comprising a tightening loop, having a first circumference in the inactive position, formed by the portion of said tubular element in said internal volume between intake and outlet openings distant by a length. The device comprises blocking means of said portion in the internal volume of said elongate element, which can be deactivated under the effect of manual traction exerted on the first or second end of said elongate element, said traction enabling the sliding of said elongate element between said orifices and correlatively the formation of the tightening loop having a second circumference in the active position, the second circumference being less than the first circumference.

20 Claims, 5 Drawing Sheets

IMPLANTABLE ATTACHMENT DEVICE, IMPLANT FOR TREATING PROLAPSE OF THE PELVIC FLOOR COMPRISING SUCH A DEVICE AND KIT COMPRISING SAID DEVICE

CROSS-REFERENCE TO RELATED APPLICATIONS

This application claims priority to French Application No. 1254648 filed May 22, 2012, the entire disclosure of which is hereby incorporated herein by reference in its entirety.

FIELD OF THE DISCLOSURE

The present invention relates to the technical field of implantable attachment devices attached to or capable of being attached to both an implant and a surgical tool, such as an instrument.

BACKGROUND OF THE DISCLOSURE

Genital prolapse is abnormal migration of one or more pelvic organs modifying the form of the vaginal walls and can lead to their exteriorisation through the urogenital orifice. The bladder, uterus and rectum are the main organs relating to this exteriorisation. These organs respectively relate to cystocele, hysterocele and rectocele. Prolapse can also relate to the vaginal fornix in the presence of a hysterectomy, Douglas' cul-de-sac (elytrocele) or associated with intestinal loops (enterocele).

There is a large variety of surgical techniques for correcting vaginal prolapse.

Surgical approaches are sufficiently varied and consist of placing a textile structure at the level of the pelvic floor. The placement of this structure textile can be done vaginally, abdominally or via laparoscopy.

A first technique is the sacrocolpopexy procedure via invasive abdominal method. It comprises suspending the neck of the uterus, the vaginal fornix, or the uterine isthmus, to the anterior longitudinal ligament in front of the promontory, at the junction of the L5-S1 vertebrae, by means of two anterior and posterior prostheses. It can be associated with complementary surgical procedures such as hysterectomy or douglassectomy, for example.

The second technique so-called "without tension" consists of interposing a knitted prosthesis based on monofilament threads made of polypropylene between the bladder and the vagina for a cystocele or between the rectum and the vagina in the case of a rectocele.

The aim of surgical treatment is to replace the suspension means (fascias, ligaments) or the retaining means (muscles of the perineum) which have failed, and most often both of them. These days, synthetic knitted "prostheses" are used. These prostheses serve to replace the failing fascias, or suspend the "fallen" organs with solid natural ligaments. This treatment can be done according to three different surgical methods:

by opening the abdomen ("laparotomy");
by celioscopy ("laparoscopy");
by entering via the vagina ("vaginally").

The efficacy of the three surgical methods in the hands of an experienced surgeon is the same. Technical simplicity, lowest complication rate, and shortest length of intervention will make the vaginal method for women in menopause or in pre-menopause, the most preferred for many surgical procedures. Celioscopy or laparotomy are plus often reserved for younger women, due to greater long-term efficacy and better resistance to substantial physical forces.

The vaginal transobturator route technique is described in patents WO 2007/016698 and WO 2005/122721. It requires the use of prosthesis of flat shape fitted with arms. The flat part is interposed between the prolapsed organ and the vagina while the arms of the prosthesis pass through the obturating holes of the pelvis. To place the prosthesis in this configuration, the surgeon uses curved or helicoidal needles, commonly known as instruments. These needles perforate the obturating holes of the exterior of the body towards the interior by passing through the skin and exiting in the anterior part of the vagina and determine the passage according to which the implant must be arranged. The arms of the prosthesis are then fixed on the tip of the needle by fastening means. The needle is then moved in the reverse direction to its passage of introduction to place the arms in the obturating holes of the pelvis, and is then withdrawn. The fastening means are also removed so that just the implant remains in the organism.

Document EP 1.399.088 B1 describes succinctly in FIGS. 7f and 7g fastening means between the needle of the instrument and an implant for treatment of prolapse of the pelvic floor. These fastening means can be a single or double knot forming an attachment loop capable of cooperating with a groove made on the distal end of the needle of the instrument, and also attached to the implant. This attachment loop does not ensure a reliable and durable bond between the needle and the implant. The loop is simply gripped manually by the surgeon, making it impossible to control the effort needed for tightening of the loop on the distal end of the needle of the instrument. This tightening effort depends on the surgeon and is therefore random and not reproducible. Also, even if the surgeon applies adequate tightening effort on the loop, it has been observed that these fastening means will relax by sliding of the threads of the loop as the needle moves into the obturating holes or the tissue. It has been observed that the loop formed relaxes as the needle is being withdrawn and causes loss of the implant to be placed; this is prohibitive for this technique, consisting of moving the implant under tension with the fastening means attached to the distal end of the needle blind in tissue or transobturating holes.

SUMMARY OF THE DISCLOSURE

The aim of the present invention is an implantable attachment device for reliable, reproducible and durable connection of an implant for treatment of prolapse of the pelvic floor with the needle of an instrument.

Another aim of the present invention is an attachment device which is simple to use, is light and has reduced bulk for moving through tissue and transobturating holes.

The aim of the present invention, according to a first aspect, is an implantable attachment device comprising an elongate tubular element which is flexible and hollow and delimits an internal volume, comprising a tightening loop, of circumference (P) in the inactive position, formed by the arrangement of a portion of said tubular element in said internal volume between intake and outlet openings distant by a length (l1), said portion having front and rear ends. The device also comprises blocking means of said portion in the internal volume of said elongate element, said blocking means being deactivated under the effect of manual traction exerted on the first or second end of said elongate element, said traction enabling the sliding of said elongate element between said orifices and correlatively the formation of a tightening loop of circumference (p) in the active position, (p) being less than (P).

Elongate tubular element means a flexible elongate element capable of forming a loop on itself, preferably a hollow textile element such as a tubular knit or a tubular braid.

Preferably, the front and rear ends of said portion are arranged respectively upstream of the intake opening and downstream of the discharge outlet.

When operating, the surgeon places the tightening loop in its inactive position on the distal end of a needle of an instrument, then exerts traction on the first or the second end of said element so as to deactivate the blocking means and forcibly tighten the tightening loop on said distal end of the needle, the loop then adopting a circumference (p) in the active position less than the initial circumference (P) in its inactive position. Deactivation of the blocking means is carried out under the effect of forced manual stress determined (daN) in under a few seconds, enabling uniform tightening of the attachment device on the distal end of the needle.

The applicant has also observed that the sliding of a portion of said elongate element in its internal volume until it forms a tightening loop of circumference (p) ensures instantaneous and durable tightening such that the implant can be moved and guided by the instrument via the attachment device according to the invention.

Of course, the unblocking force (daN) of the blocking means is determined so as not to be too high and avoid exerting tension on the tissue or the obturating holes, since traction exerted on one of the ends of said elongate element is carried out when the needle of the instrument is moved through the tissue and the transobturating holes.

The passage of the tightening loop from an inactive position to an active position is quasi-instantaneous, ensuring the reliability and duration of the connection of the attachment device at the distal end of the needle of the instrument.

In a variant, the blocking means comprise a coating made of at least one polymer applied to the external surface and the periphery of the elongate element over the length (l1) separating the intake and outlet openings.

The rupture of the coating caused by traction exerted by the surgeon on the first or second end of said elongate element moves the tightening loop from an inactive position to an active position quasi-instantaneously.

In a variant, the mass of the coating is less than or equal to 20 g/meter of said flexible tubular element.

It is not actually necessary to have too great a quantity of coating between the intake and outlet openings, the aim simply being to prevent natural sliding of said portion of said element in its internal volume and to engender some resistance obliging the surgeon to exert effort of a few kilos only to tighten the tightening loop on the distal end of the needle of the instrument.

In a variant, the blocking means comprise at least one first sphere in at least one polymer blocking the intake opening, said sphere being arranged about the front end of said portion and arranged such that the manual traction exerted on the first or the second end of said elongate element causes forced passage of said first sphere in the internal volume of said elongate element until it exits via said discharge outlet.

In a variant, the blocking means comprise a second sphere in at least one polymer blocking the discharge outlet, said sphere being arranged about the rear end of said portion.

In a variant, said material polymer is selected alone or in combination from the following polymers: polydimethysiloxane (PDMS), polyurethane, polymer lactic acid L or D shape (PLLA or PLDA), polyamide (PA 66 especially).

The polymer materials forming the spheres or said spheres and/or said coating can be of the same kind.

In a variant, the tightening loop has a circumference (P) in the inactive position of less than 5 cm, preferably less than 3 cm.

The tightening loop has a circumference greater than 0 cm, preferably greater than 0.5 cm.

The applicant has observed that the sliding of said elongate element on itself ought not to be done over too great a distance to produce quasi-instantaneous and therefore reliable tightening.

In a variant, the length (l1) separating the intake and outlet openings is less than or equal to 3 cm, preferably less than or equal to 1 cm. The length (l1) is greater than 0 cm.

This arrangement also contributes to ensuring quasi-instantaneous and reliable tightening.

In a variant, the elongate element is a textile element, in particular a braid or a knit, comprising one or more multifilament threads and/or one or more monofilament threads.

The presence of threads causes more friction during sliding of said elongate element on itself and even improves the reliability and holding over time of the tightening loop in the active position on the distal end of the needle of the instrument.

In a variant, the elongate element has a mass per unit of less than or equal to 25 g/meter, preferably less than or equal to 15 g/meter, and more preferably less than or equal to 2 g/meter.

The elongate element according to the invention is very light and therefore minimally invasive.

In a variant, the traction exerted on the first or the second end enabling deactivating of the blocking means is less than or equal to 4 daN, preferably less than or equal to 2.5 daN.

Preferably, the traction exerted on the first or the second end is greater than 0.5 daN.

The applicant has determined that these intervals of tightening forces produce quasi-instantaneous tightening without exerting tension on the needle and therefore on the tissue or the transobturating holes in which said needle is arranged.

The aim of the present invention, according to a second aspect, is an implant for treatment of prolapse of the pelvic floor, especially for curing hysterocele, cystocele or rectocele, configured so as to present a central supporting part and at least two lateral anchoring parts arranged on either side of said central part comprising an attachment device according to any one of the variant embodiments described hereinabove. Advantageously, the second end of said elongate element is attached to or capable of being attached to one of the two lateral anchoring parts.

Preferably, the second end of said elongate element is attached to at least one lateral anchoring part by cutting, splicing or by means of one or more knots between said end and said lateral part.

The aim of the present invention, according to a third aspect, is a kit comprising an attachment device according to any one of the preceding variant embodiments, and an instrument.

Said instrument comprises a needle provided according to its distal end with an attachment zone capable of cooperating with the tightening loop of said attachment device.

Preferably, the kit according to the invention also comprises an implant for treatment of prolapse of the pelvic floor according to one of the embodiment variants described hereinabove.

In a variant, the attachment zone has a length (l2) and comprises front and rear stops capable of blocking the tightening loop of said elongate element in said attachment zone when the tightening loop is in the active position.

Preferably, the length (l2) is greater than or equal to 3 mm, more preferably greater than or equal to 5 mm, more preferably less than or equal to 20 mm.

Preferably, the attachment zone is cylindrical in shape and has a circumference less than or equal to the circumference of the attachment loop in its active position (p). In fact, the cylindrical shape of the attachment zone avoids the presence of a ridge or surface which might be blunt for said elongate element.

BRIEF DESCRIPTION OF THE DRAWINGS

The present invention will be more clearly understood from the following description of two embodiments cited as non-limiting, and illustrated by the following figures, attached to the present document.

DETAILED DESCRIPTION

Figure 1:
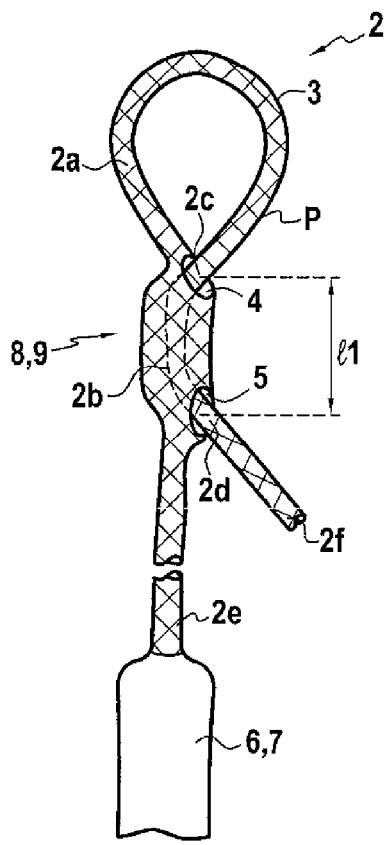
FIG. 1 is a schematic and perspective representation of a first embodiment of an attachment device according to the invention according to a first variant.

The first variant of the first example of an attachment device 1 illustrated in FIG. 1 comprises an elongate tubular element 2 which is flexible and hollow, delimiting an internal volume 2a comprising a tightening loop 3, of circumference (P) in the inactive position, formed by the arrangement of a portion 2b of said tubular element 2 in said internal volume 2a between intake 4 and outlet 5 openings distant by a length (l1), said portion 2b having front 2c and rear 2d ends.

Preferably, the length (l1) separating the intake openings 4 and outlet 5 is less than or equal to 3 cm, preferably less than or equal to 1 cm.

The attachment device 1 comprises a tightening loop 3 in the inactive position having a circumference (P) less than or equal to 5 cm, preferably less than or equal to 3 cm.

Said elongate element 2 is provided with first 2f and second 2e ends. In this example, the first end 2f is introduced to the internal volume 2a of the elongate element 2 via the intake opening 4 and exits therefrom via the discharge outlet 5, forming a portion 2b of said elongate element 2 housed in its internal volume 2a. The first end 2f is in this precise example is free and can be gripped by the surgeon to cause sliding of the portion 2b in the internal volume 2a of the elongate element 2. The second end 2e of the elongate element 2 is illustrated here attached to a lateral anchoring part 6 of an implant 7 according to the invention. Any connecting means known to the person skilled in the art can be utilised: splicing and/or knot or fusion of the second end of the elongate element with the end of the lateral anchoring part 6.

The attachment device 1 comprises blocking means 8 of said portion 2b in the internal volume 3 of said elongate element 2. In this precise example, the blocking means 8 comprise a coating 9 of at least one polymer applied to the external surface and the periphery of the elongate element 2 over the length (l1) separating the intake 4 and outlet 5 openings. Preferably, said at least one polymer is selected from polyurethane, polydimethylsiloxane (PDMS), polylactic acid of L or D shape (PLLA or PLDA), or a base of polyamide, such as PA 66.

Preferably, the resistance of the bond (i.e. the resistance to breaking measured in daN) between the second end 2e of the elongate element 2 and the lateral part 6 must be greater than the unblocking force necessary for deactivation of the blocking means 8.

Preferably, the mass per unit of the coating 9 relative to the length of said elongate element 2 is less than or equal to 20 g/meter of said elongate element 2, preferably less than or equal to 15 g/meter.

Preferably, said elongate element 2 is a knitted or braided textile element and has a linear mass less than 10 g/meter, preferably less than 5 g/meter, and more preferably less than or equal to 2 g/meter.

Preferably, the elongate element 2 is a knitted or braided textile element with multifilament threads and/or monofilament threads, preferably multifilament threads. Said threads are preferably selected from the following polymers, singly or in combination: polyethylene terephthalate, polypropylene, PLLA or PLDA, polyethylene.

The titration of the threads is preferably less than or equal to 300 dtex, preferably less than or equal to 150 dtex.

The elongate element 2 is preferably a braid produced by the braiding of six multifilament threads, especially made of polyethylene terephthalate, having a titration less than or equal to 150 dtex.

Figure 2:
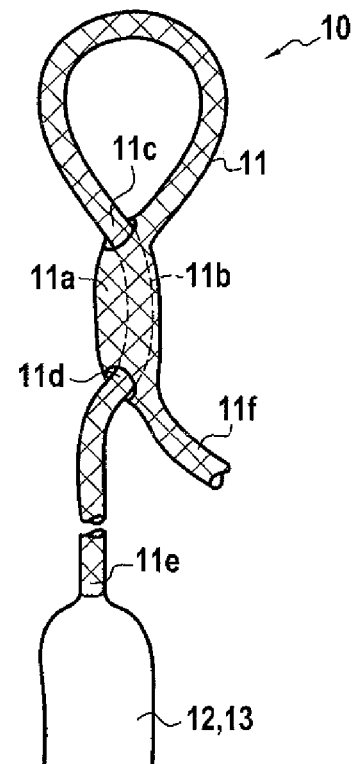
FIG. 2 is a schematic and perspective representation of a second variant of the attachment device illustrated in FIG. 1.

The second variant of the first example of an attachment device 10 illustrated in FIG. 2 differs from the first variant 1 illustrated in FIG. 1 in that the portion 11b housed in the internal volume 11a of the elongate element 11 is reversed, such that it is necessary to exert traction on the second end 11e connected to at least one lateral anchoring part 12 of the implant 13 according to the invention to produce sliding of the portion 11b in said internal volume 11a.

Figure 3:
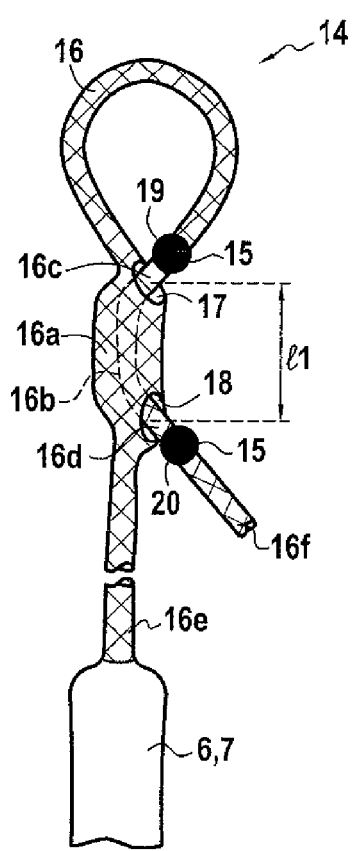
FIG. 3 is a schematic and perspective representation of a second example of an attachment device according to the invention according to a first variant, FIG. 4 a schematic and perspective representation of a second variant of the attachment device illustrated in FIG. 3.

The first variant of the second example of an attachment device 14 illustrated in FIG. 3 differs from the first example 1 by the blocking means 15 it comprises. In fact, the elongate element 16 comprises no coating placed on its periphery between the intake 17 and outlet 18 openings on the length (l1) but first 19 and second 20 spheres in at least one polymer blocking respectively the intake openings 17 and outlet 18. The first 19 and second 20 spheres are arranged respectively about the front 16c and rear 16d ends of the portion 16b of the elongate element 16 housed in its internal volume 16a, and arranged such that manual traction exerted on the first end 16f of said elongate element 16 causes the forced passage of the first sphere 19 in the internal volume 16a of said elongate element 16 until it exits via said discharge outlet 18.

Figure 4:
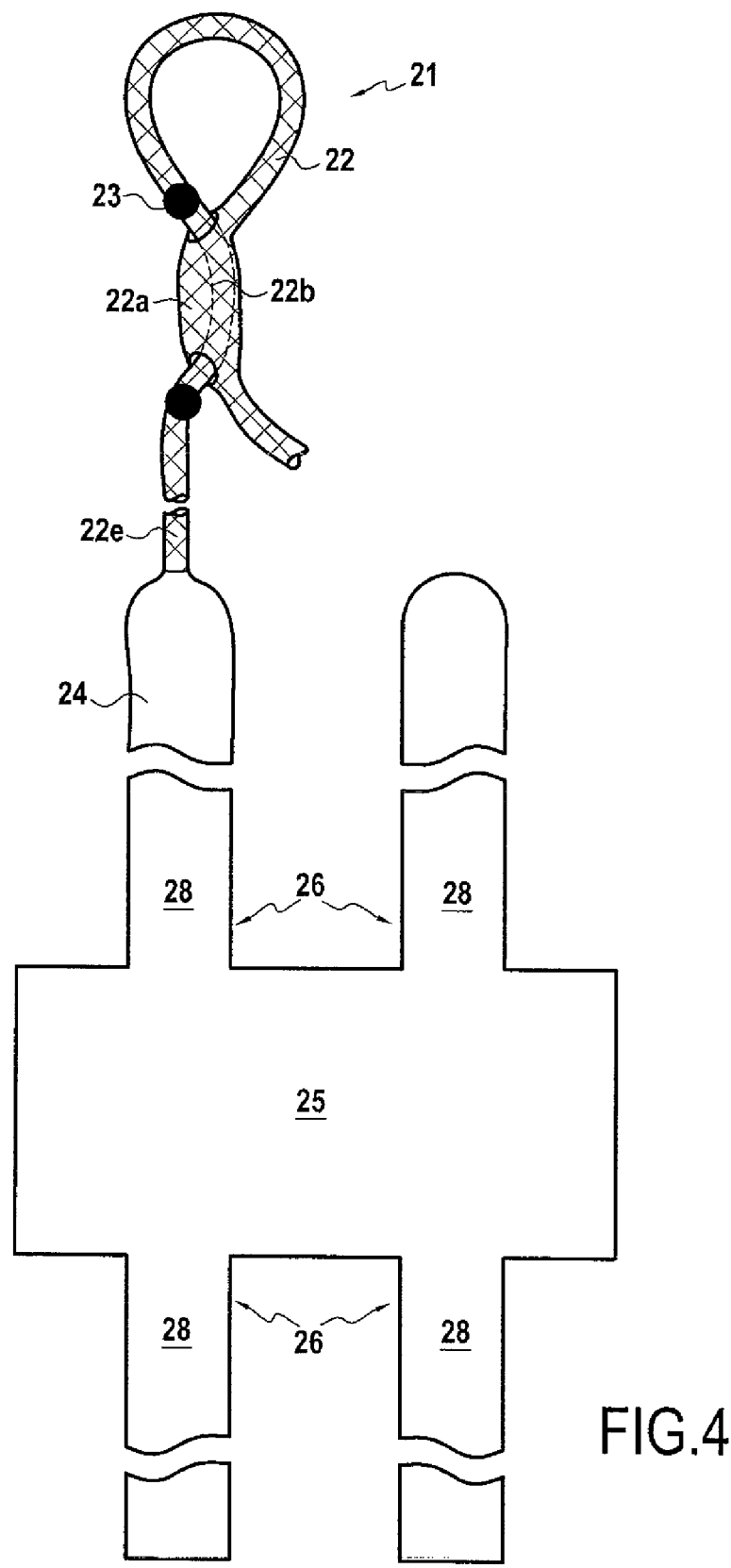

The second variant of the attachment device 21 illustrated in FIG. 4 differs from the first variant 14 illustrated in FIG. 3 in that the portion 22b of the elongate element 22 housed in its internal volume 22a is reversed, involving the surgeon having to exert traction on the second end 22e of the elongate element 22 to effect forced passage of the first sphere 23 in said internal volume 22a.

FIG. 4 also illustrates an entire implant 24 for the treatment of prolapse of the pelvic floor comprising a central supporting part 25 from which two pairs 26, 27 of lateral anchoring parts 28 project, whereof at least one is attached to the second end 22e of the elongate element 22.

The coating can be optionally combined with a first sphere blocking the intake opening, and optionally again with a second sphere blocking the discharge outlet, at the moment when the traction force necessary for shifting the tightening loop from an inactive position to an active position is less than or equal to 4 daN, preferably less than or equal to 2.5 daN. The traction force is preferably greater than 0.5 daN to effect shifting from an inactive position to an active position for the tightening loop, quasi-instantaneous, ensuring reliable and reproducible tightening of the tightening loop.

Figure 5:
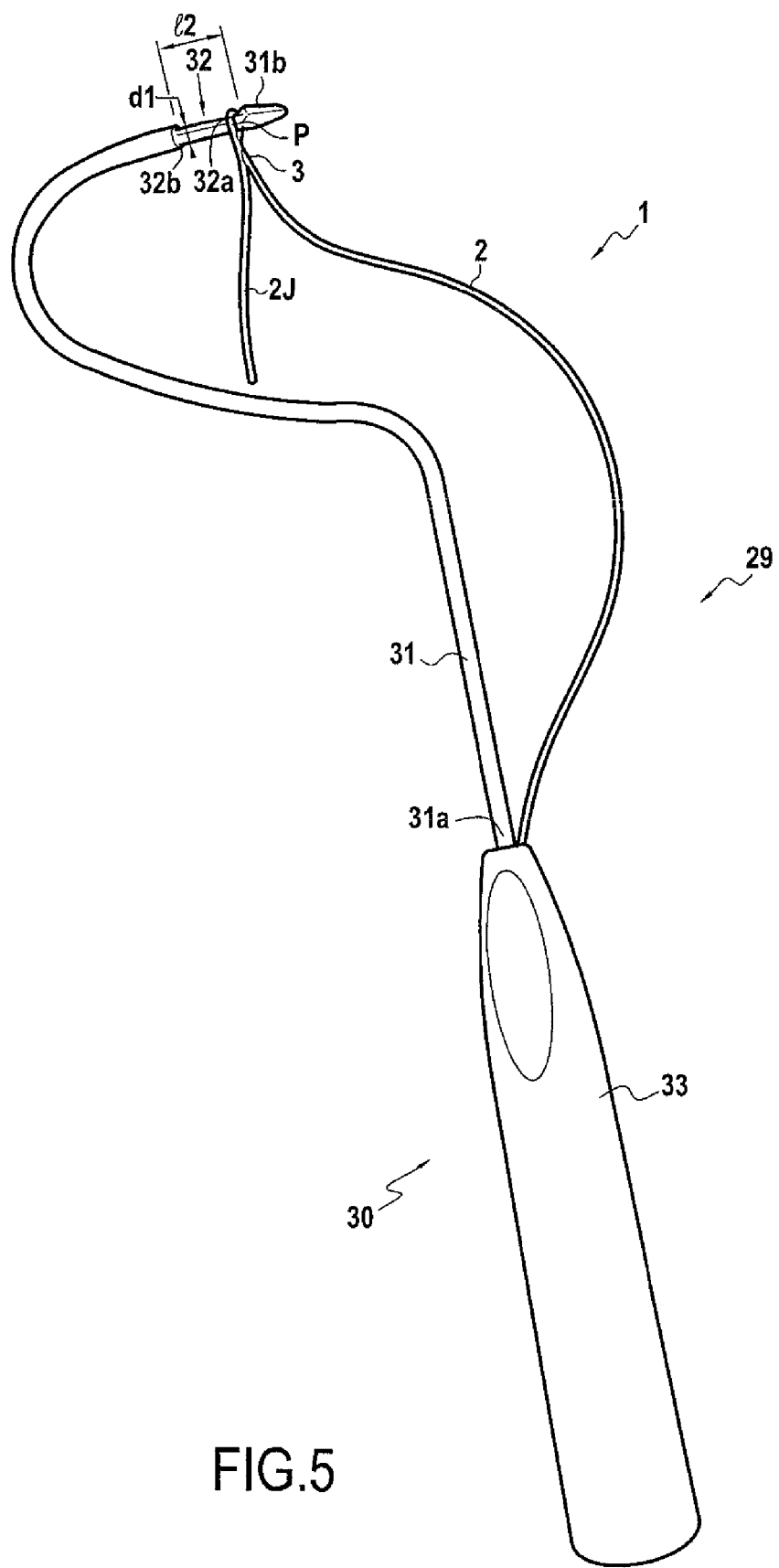
FIG. 5 is a schematic and perspective representation of a kit according to the invention comprising an instrument and the first example of an attachment device illustrated in FIG. 1 in the inactive position.

FIG. 5 illustrates a kit 29 according to the invention comprising an instrument 30 including a needle 31 provided with an attachment zone 32 capable of cooperating with the tightening loop 3 of the tightening device 1 represented in FIG. 1 in its inactive position.

The instrument 30 comprises a handle 33 and a curved needle 31 comprising proximal 31a and distal 31b ends.

The attachment zone 32 is arranged according to the distal end 31b of the needle 31 and has a length (l2) and front 32a and rear 32b stops for the tightening loop 3 when the latter is threaded onto the attachment zone 32.

In this precise example, the attachment zone 32 is cylindrical in shape and comprises an external diameter d1.

Quite evidently, the circumference in the inactive position of the tightening loop 3 is less than or equal to (P), preferably less than or equal to 5 cm, and more preferably less than or equal to 3 cm, and in all cases greater than n (pie)*d1.

Figure 6:
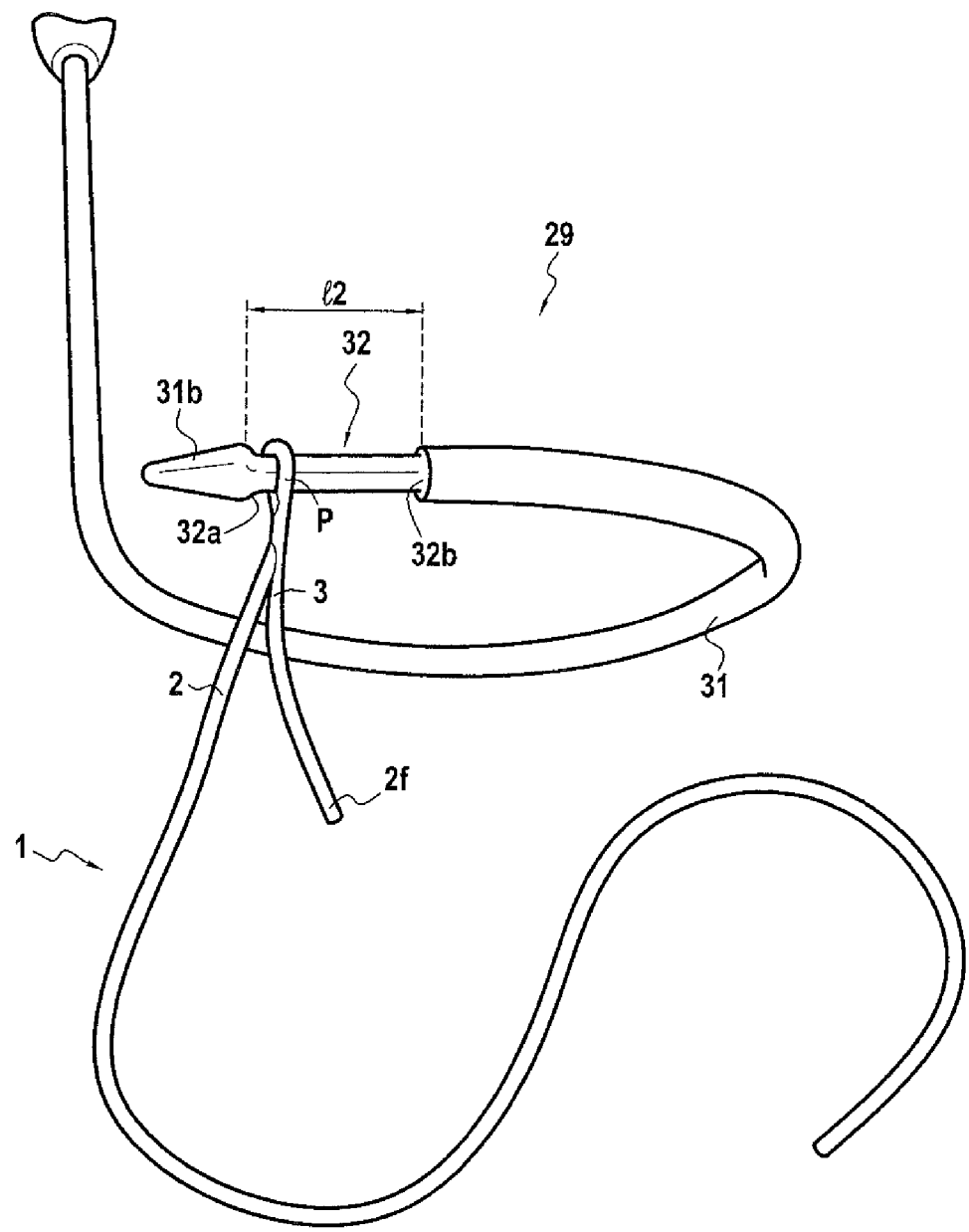
FIG. 6 is a schematic and perspective representation of the kit illustrated in FIG. 5 in which the attachment device is in the active position.

When operating, and after he has moved the needle 31 in the tissue and/or the transobturating holes and has the tightening loop 3 in the inactive position on the attachment zone 32, the surgeon exerts traction by jerking on the first end 2f of the elongate element 2 to deactivate the blocking means 8, 9, in this case to break the coating 9 and have the tightening loop 3 adopt its circumference in the active position (p), such as illustrated in FIG. 6. The tightening is quasi-instantaneous, ensuring its efficacy.

Also, the tightening decreases the length between the intake 4 and outlet 5 openings due to the sliding of said elongate element 2, which improves its holding over time.

Since the elongate element 2 is very fine and is made of textile material, the friction of the threads during sliding also contributes to blocking the tightening loop 3 about the tightening zone 32 of the needle 31.

When the blocking means 8, 9, 19, 20, 23 comprise a first sphere 19, 23, the latter keep the intake and outlet openings close in the active position.

Figure 7:
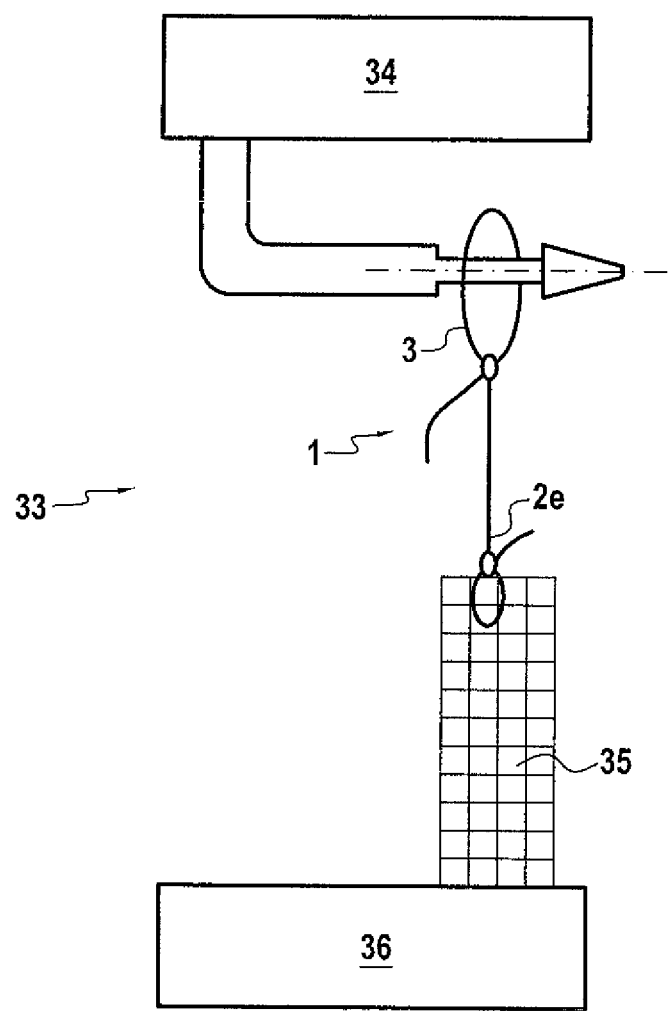
FIG. 7 illustrates a method for measuring the force necessary for deactivating the blocking means according to the invention.

FIG. 7 illustrates a traction bench 33, for example of brand LLOYD LR X, on which the force necessary for deactivating the blocking means 8, 9 of the attachment device 1 illustrated in FIG. 1 is measured. The tightening loop 3 in the inactive position is arranged about an organ illustrating the distal end 31b of the needle 31 of the instrument 30 according to the invention, said organ being held between upper tightening jaws 34. The second end 2e of the attachment device 1 is connected to a textile 35 having a width of 1 cm and a height of 10 cm. The textile 35 is as such pinched between lower tightening jaws 36. The height separating the lower jaws 36 from the upper jaws 34 is 20 cm. The traction speed is by way of example 100 mm/minute.

The invention claimed is:

1. An implantable attachment device comprising an elongate tubular element which is flexible and hollow delimiting an internal volume comprising a tightening loop, having a first circumference in the inactive position, formed by the arrangement of a portion of said tubular element in said internal volume between intake and outlet openings distant by a length, said portion having front and rear ends, and wherein the device comprises a blocking device of said portion in the internal volume of said elongate element, said blocking device being deactivated under the effect of manual traction exerted on the first or second end of said elongate element, said traction enabling the sliding of said elongate element between said orifices and correlatively the formation of the tightening loop having a second circumference in the active position, the second circumference being less than the first circumference, wherein the blocking device comprises a coating in at least one polymer applied to the external surface and the periphery of the elongate element over the length separating the intake and outlet openings.

2. The attachment device according to claim 1, wherein the mass of the coating is less than or equal to 20 g per meter of said tubular flexible element.

3. The attachment device according to claim 1, wherein said polymer material is selected alone or in combination from the following polymers: polydimethysiloxane (PDMS), polyurethane, lactic acid polymer of L or D shape (PLLA or PLDA), and polyamide.

4. The attachment device according to claim 3, wherein said polyamide is PA 66.

5. The device according to claim 1, wherein the tightening loop has a circumference in the inactive position of less than 5 cm.

6. The device according to claim 5, wherein the tightening loop has a circumference in the inactive position of less than 3 cm.

7. The device according to claim 1, wherein the length separating the intake and outlet openings is less than or equal to 3 cm.

8. The device according to claim 7, wherein the length separating the intake and outlet openings is less than or equal to 1 cm.

9. The device according to claim 1, wherein the elongate element is a textile element, in particular a braid or a knit, comprising one or more multifilament threads and/or one or more monofilament threads.

10. An implantable attachment device comprising:
an elongate tubular element which is flexible and hollow delimiting an internal volume comprising a tightening loop, having a first circumference in the inactive position, formed by the arrangement of a portion of said tubular element in said internal volume between intake and outlet openings distant by a length, said portion having front and rear ends, and
wherein the device comprises a blocking device of said portion in the internal volume of said elongate element, said blocking device being deactivated under the effect of manual traction exerted on the first or second end of said elongate element, said traction enabling the sliding of said elongate element between said orifices and correlatively the formation of the tightening loop having a second circumference in the active position, the second circumference being less than the first circumference; and
wherein the blocking device comprises at least one first sphere in at least one polymer blocking the intake opening, said at least one first sphere being arranged about the front end of said portion, and arranged such that manual traction exerted on the first or the second end of said elongate element causes the forced passage of said at least one first sphere in the internal volume of said elongate element until it exits via said discharge outlet.

11. The device according to claim 10, wherein the blocking device comprises a second sphere in at least one polymer blocking the discharge outlet, said second sphere being arranged about the end rear of said portion.

12. The attachment device according to claim 11, wherein said polymer material is selected alone or in combination from the following polymers: polydimethysiloxane (PDMS), polyurethane, lactic acid polymer of L or D shape (PLLA or PLDA), and polyamide.

13. The attachment device according to claim 12, wherein said polyamide is PA 66.

14. The device according to claim 10, wherein the elongate element is a textile element, in particular a braid or a knit, comprising one or more multifilament threads and/or one or more monofilament threads.

15. An implantable attachment device comprising:
an elongate tubular element which is flexible and hollow delimiting an internal volume comprising a tightening loop, having a first circumference in the inactive position, formed by the arrangement of a portion of said tubular element in said internal volume between intake and outlet openings distant by a length, said portion having front and rear ends, and
wherein the device comprises a blocking device of said portion in the internal volume of said elongate element, said blocking device being deactivated under the effect of manual traction exerted on the first or second end of said elongate element, said traction enabling the sliding of said elongate element between said orifices and correlatively the formation of the tightening loop having a second circumference in the active position, the second circumference being less than the first circumference; and
wherein the elongate element has a mass per unit less than or equal to 25 g/meter.

16. The device according to claim 15, wherein the elongate element has a mass per unit less than or equal to 15 g/meter.

17. An implantable attachment device comprising:
an elongate tubular element which is flexible and hollow delimiting an internal volume comprising a tightening loop, having a first circumference in the inactive position, formed by the arrangement of a portion of said tubular element in said internal volume between intake and outlet openings distant by a length, said portion having front and rear ends, and
wherein the device comprises a blocking device of said portion in the internal volume of said elongate element, said blocking device being deactivated under the effect of manual traction exerted on the first or second end of said elongate element, said traction enabling the sliding of said elongate element between said orifices and correlatively the formation of the tightening loop having a second circumference in the active position, the second circumference being less than the first circumference; and
wherein the traction exerted on the first or the second end to deactivate the blocking device is less than or equal to 4 daN.

18. The device according to claim 17, wherein the traction exerted on the first or the second end to deactivate the blocking device is less than or equal to 2.5 daN.

19. An implant for the treatment of prolapse of the pelvic floor, especially for curing hysterocele, cystocele or rectocele, configured so as to present a central supporting part and at least two lateral anchoring parts arranged on either side of said central part, wherein the implant comprises:
an attachment device comprising:
an elongate tubular element which is flexible and hollow delimiting an internal volume comprising a tightening loop, having a first circumference in the inactive position, formed by the arrangement of a portion of said tubular element in said internal volume between intake and outlet openings distant by a length, said portion having front and rear ends, and
wherein the device comprises a blocking device of said portion in the internal volume of said elongate element, said blocking device being deactivated under the effect of manual traction exerted on the first or second end of said elongate element, said traction enabling the sliding of said elongate element between said orifices and correlatively the formation of the tightening loop having a second circumference in the active position, the second circumference being less than the first circumference;
wherein the blocking device comprises a coating in at least one polymer applied to the external surface and the periphery of the elongate element over the length separating the intake and outlet openings; and
wherein the second end of said elongate element is attached to or capable of being attached to one of the lateral anchoring parts.

20. A kit comprising:
an implantable attachment device comprising:
an elongate tubular element which is flexible and hollow delimiting an internal volume comprising a tightening loop, having a first circumference in the inactive position, formed by the arrangement of a portion of said tubular element in said internal volume between intake and outlet openings distant by a length, said portion having front and rear ends, and
wherein the device comprises a blocking device of said portion in the internal volume of said elongate element, said blocking device being deactivated under the effect of manual traction exerted on the first or second end of said elongate element, said traction enabling the sliding of said elongate element between said orifices and correlatively the formation of the tightening loop having a second circumference in the active position, the second circumference being less than the first circumference; and
an instrument comprising a needle provided at its distal end with an attachment zone capable of cooperating with the tightening loop of said attachment device, wherein the attachment zone has a length and comprises front and rear stops capable of blocking the tightening loop of said elongate element in said attachment zone when the tightening loop is in the active position.

* * * * *